(12) United States Patent
Benedetti et al.

(10) Patent No.: US 7,381,718 B2
(45) Date of Patent: Jun. 3, 2008

(54) METHOD FOR PREPARING OESTROGEN DERIVATIVES

(75) Inventors: Francoise Benedetti, Rosny sous Bois (FR); Alain Mazurie, Vanjours (FR); Francois Nique, Le Perreaux (FR); Denis Prat, Pantin (FR); Christian Wehrey, Villemomble (FR)

(73) Assignee: Aventis Pharma S.A., Antony (FR)

( * ) Notice: Subject to any disclaimer, the term of this patent is extended or adjusted under 35 U.S.C. 154(b) by 663 days.

(21) Appl. No.: 10/480,618

(22) PCT Filed: Jun. 12, 2002

(86) PCT No.: PCT/FR02/02001

§ 371 (c)(1), (2), (4) Date: Jan. 12, 2004

(87) PCT Pub. No.: WO02/100880

PCT Pub. Date: Dec. 19, 2002

(65) Prior Publication Data

US 2004/0171595 A1  Sep. 2, 2004

(30) Foreign Application Priority Data

Jun. 13, 2001 (FR) .................................. 01 07711

(51) Int. Cl.
*A61K 31/58* (2006.01)
*C07J 1/00* (2006.01)
*C07J 43/00* (2006.01)

(52) U.S. Cl. ..................... 514/176; 552/626; 540/113

(58) Field of Classification Search ................ 552/626; 540/113; 514/176

See application file for complete search history.

(56) References Cited

FOREIGN PATENT DOCUMENTS

| EP | 0057115 | 8/1982 |
|---|---|---|
| EP | 0097572 | 1/1984 |
| EP | 0245170 | 11/1987 |
| EP | 0384842 | 8/1990 |
| FR | 2377418 | 8/1978 |
| FR | 2377419 | 8/1978 |
| FR | 2640977 | 6/1990 |
| WO | 9630390 | 10/1996 |
| WO | 9828324 | 7/1998 |
| WO | 9845316 | 10/1998 |
| WO | 9925725 | 5/1999 |

*Primary Examiner*—Barbara P. Badio
(74) *Attorney, Agent, or Firm*—Charles A. Muserlian

(57) ABSTRACT

A process for the preparation of compounds of formula (I)

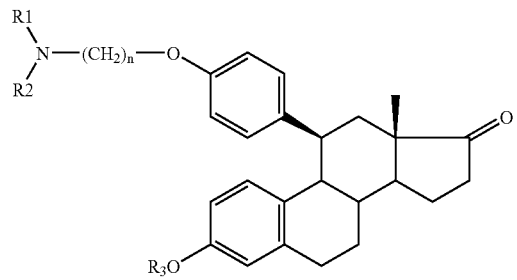

in which
$R_1$, $R_2$, $R_3$ and n are defined as indicated in the description, use of said compounds as intermediates for the preparation of estrogen derivatives as well as the intermediates of this process.

11 Claims, No Drawings

METHOD FOR PREPARING OESTROGEN DERIVATIVES

This application is a 371 of PCT/FR02/02001 filed Jun. 12, 2002.

A subject of the present invention is a process for the preparation of estrogen steroids as well as the intermediates of this process.

Osteoporosis is a bone disease which affects 50 million people world-wide, more particularly women. Its development is linked to age and most often commences after the menopause. This disease is characterized by a reduction in bone density, leading to deformations, compacted vertebrae and finally spontaneous fractures. Osteoporosis therefore represents a serious public health concern. The principal treatment consists of regularly taking estradiol which reduces bone loss, which can however be accompanied by certain side effects (bleeding, hot flushes, risk of breast cancer etc.). A new series of molecules called SERMs (Selective Estrogen Receptor Modulator) allows the treatment of osteoporosis whilst avoiding certain side effects. (WO098/45316, WO099/67274, WO098/28324, WO099/25725, EP605193).

The subject of the present Application is the development of a new process for the preparation of a key intermediate (compound of formula I), and the use of this intermediate in the synthesis of certain estrogen derivatives having a dissociated activity.

A subject of the invention is a process for the preparation of compounds of formula (I):

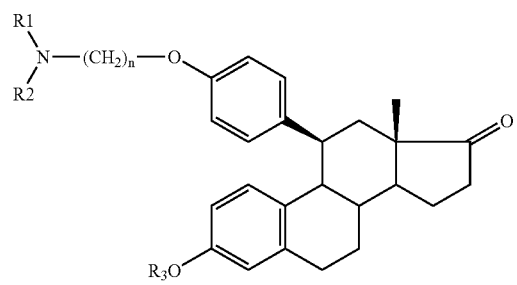

(I)

in which:
either $R_1$ and $R_2$, identical or different, represent a benzyl group or an linear, branched or cyclic alkyl, alkenyl or alkynyl radical containing from 1 to 8 carbon atoms,
or $R_1$ and $R_2$ form together with the nitrogen atom which carries them an aromatic or non-aromatic, saturated or unsaturated heterocycle with 5 to 6 members, optionally containing from 1 to 3 additional heteroatoms, and optionally connected to another ring,
$R_3$ represents a hydrogen atom or a protective group of the hydroxy function,
n is an integer from 2 to 8,
characterized in that a compound of formula (II)

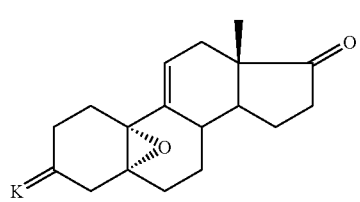

(II)

K representing a protected ketone function in particular in the form of ketal, thioketal or mixed ketal, is treated with a silylation agent in the presence of a base, in order to obtain the silylated enol of formula (III):

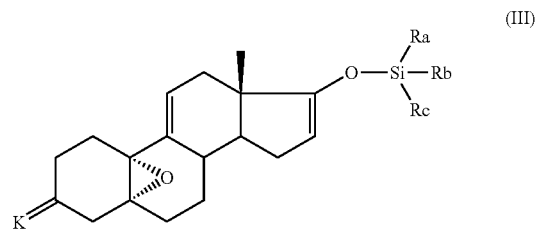

(III)

in which Ra, Rb and Rc, identical or different, represent an alkyl radical containing from 1 to 4 carbon atoms or a phenyl radical,
which is reacted with
an organocuprate derivative, derived from the organometallics of formulae $R_5MgHal$ or $R_5Li$, Hal being a halogen atom and generated in a catalytic or stoichiometric fashion, in which $R_5$ represents the

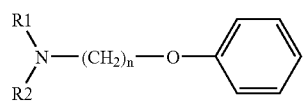

group,
n, $R_1$ and $R_2$ being as defined above, the bond being made at the level of the phenyl, in order to obtain a compound of formula (III') which is isolated or non-isolated:

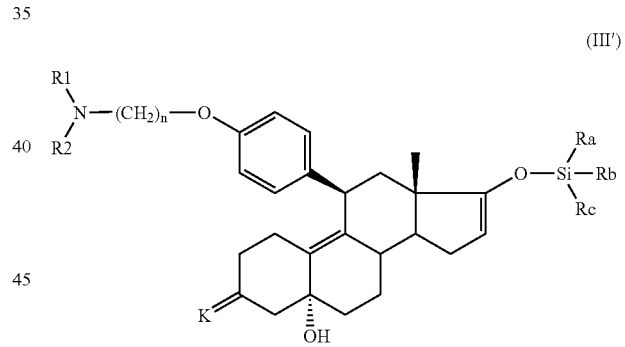

(III')

then a deprotection agent
in order to obtain a compound of formula (IV)

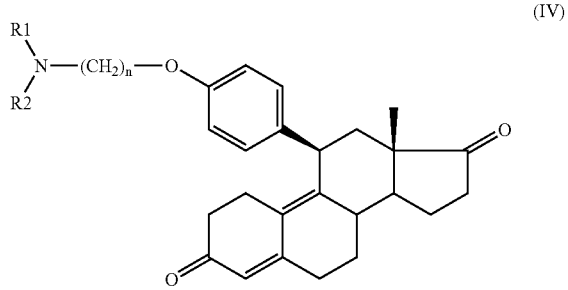

(IV)

which is treated with an aromatization agent in order to obtain the expected compound of formula (I) which, if appropriate, is subsequently deprotected in order to obtain a compound of formula (I) with R₃ representing a hydrogen atom.

As examples of linear or branched alkyl radicals containing from 1 to 8 carbon atoms, the methyl, ethyl, propyl, butyl, pentyl, hexyl, octyl radicals, and the n-isomers of these radicals, isopropyl, isobutyl, isopentyl, neopentyl, isohexyl, 3-methylpentyl, sec-butyl, tert-butyl, tert-pentyl can be mentioned. The preferred alkyl radicals are methyl, ethyl, n-propyl, isopropyl, n-butyl, iso-butyl, sec-butyl and tert-butyl.

As examples of cyclic alkyl radicals, the cyclopropyl, cyclobutyl, cyclopentyl and cyclohexyl, cycloheptyl or cyclononyl radicals can be mentioned, which can be substituted, for example, by an alkyl group containing from 1 to 4 carbon atoms. Preferably, the substituted cycloalkyl groups are 4-methylcyclohexyl and 2,3-dimethylcyclopentyl.

As examples of alkenyl radicals, the vinyl, 1-propenyl, allyl, butenyl or 3methyl-2-butenyl radicals can be mentioned. As examples of alkynyl radicals the ethynyl, 1-propynyl or propargyl radicals can be mentioned. Of course these alkenyl or alkynyl radicals contain at least 2 carbon atoms and are linked to the nitrogen atom via a —CH₂- group.

As examples of protective groups which can be represented by R₃, a ($C_1$-$C_6$)-alkyl, ($C_1$-$C_6$)-alkyl-CO-group such as CH₃CO or a benzoyl, benzyl, phenyl-($C_1$-$C_6$)-alkyl group such as benzyl can in particular be mentioned, as well as all the protective groups known to a person skilled in the art for example those described in Greene, Wuts, Protective Group in Organic Synthesis, Wiley, 1991. Preferably R3, as a protective group, is an acyl group.

As examples of protective groups of the keto in position 3 of the steroid which can be represented by =K the following can in particular be mentioned:
the cyclic ketals such as —O—(CH₂)$_m$—O—, —O—(CH₂)$_m$—S—, —S—(CH₂)$_m$—S—, —O—CH₂—C($c_{1-4}$-alkyl)₂—CH₂—O—,
the acyclic ketals such as (CH₃O)₂, (EtO)₂
as well as all the protective groups of the keto group known to a person skilled in the art for example those described in Greene, Wuts, Protective Group in Organic Synthesis, Wiley, 1991.

Preferably, =K is a cyclic ketal and, in particular a 3,3-ethylenedioxy group.

Hal represents a halogen and preferably chlorine or bromine.

Ra, Rb and Rc preferably represent a methyl group.

As silylation agents, all the agents capable of silylating enols or enolates known to a person skilled in the art, and, if appropriate, mentioned in the monograph Van Look, G.; Simchen, G.; Heberle, J., Silylating Agents; Fluka Chimica, Fluka Chemie AG; Buchs, Switzerland, 1995, can be mentioned. They can be the following silylation agents:

Me₃Si—N=C(Me)—O—SiMe₃ N,O-bis(trimethylsylyl)acetamide
Me₃Si—NH—CO₂—SiMe₃ N,O-bis(trimethylsylyl)carbamate
(Me₃Si)₂N—CHO N,N'-bis(trimethylsilyl)formamide
(Me₃SiO)₂SO₂ bis(trimethylsilyl)sulphate
F₃C—C(OSiMe₃)=N—SiMe₃ N,O,bis(trimethylsilyl)trifluoroacetamide
(Me₃SiNH)₂CO N,N'bis(trimethylsilyl)urea
EtS—SiMe₃ Ethylthiotrimethylsilane
Me₃Si—CH₂—CO₂Et Ethyltrimethylsilylacetate)
Me₃Si—CH₂—CO₂Me Methyltrimethylsilylacetate
Me₃Si—SiMe₃ Hexamethyldisilane
CH₃—C(OSiMe₃)=CH₂ Isopropenyloxytrimethylsilane
(CH₃)₂C=C(OMe)(OSiMe₃) 1 methoxy 2-methyl-1-trimethylsilyloxypropene
CH₃CO—N(Me)—SiMe₃ N-methyl N trimethylsilylacetamide
CF₃CO—N(Me)—SiMe₃N-methyl N trimethylsilyltrifluoroacetamide
C₃F₇—CO—N(Me)—SiMe₃ N-methyl N trimethylsilylheptafluorobutyramide
Me₃SiBr Trimethylbromosilane
Me₃Si—I Trimethyliodosilane
PhSO₃—SiMe₃ Trimethylsilylbenzenesulphonate
MeSO₃SiMe₃ Trimethylsilylmethanesulphonate
Me₃Si—CN Trimethylsilyl cyanide
Trimethylsilylimidazole
C₄F₉SO₃SiMe₃ Trimethylsilyl-nonaflate
CF₃SO₃SiMe₃ Trimethylsilyl-triflate
CF₃—CO₂—SiMe₃ Trimethylsilyl-trifluoroacetate
CCl₃—CO₂—SiMe₃ Trimethylsilyl-trichloroacetate
tBuSiMe₂Cl t-Butyldimethylchlorosilane
tBuSiPh₂ Cl t-Butyldiphenylchlorosilane
PhSiMe₂Cl dimethylphenylchlorosilane
Ph₂SiMeCl diphenylmethylchlorosilane
iPrSiMe₂Cl Isopropyldimethylchlorosilane
Me₃Si—NHSiMe₃ Hexamethyldisilazane
nBU₃SiCl Tributylchlorosilane
Et₃SiCl Triethylchlorosilane
(iPr)₃SiCl Triisopropylchlorosilane
Ph₃SiCl Triphenylchlorosilane
(nPr)₃SiCl Tripropylchlorosilane.

This silylation reaction is generally carried out in the presence of a strong base such as Li-HMDS ((Me₃Si)₂N—Li), LDA ((iPr)₂N—Li), a tertiary amine such as TEA (triethylamine), Na-naphthalene, pyridine and its derivatives such as DMA (Dimethylaminopyridine), urea, DBU, imidazole, potassium hydride, sodium hydride, n-BuLi, tBuOK or also t-AmONa, DBN and others.

The silylation reaction is generally carried out in two stages:

1) enolization of the compounds of formula (II) in the presence of a strong base such as LDA in order to obtain the corresponding enolate of formula (II'):

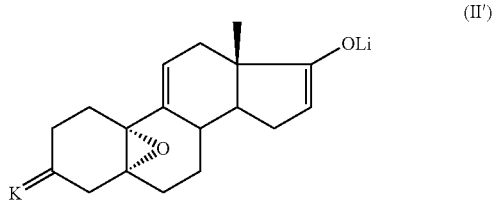

addition of the silylation agent such as chlorotrimethylsilane.

However, not all these silylation agents necessarily require the enolate of the compounds of formula (II) to be produced beforehand.

The solvents used are known to a person skilled in the art for this type of reaction (J K Rasmussen, Synthesis 91 (1977), E. Colvin Silicon in Organic synthesis Butterworth (1981); WP Weber "silicon reagent for Organic synthesis", Springer Verlag (1983) P. Brownbridge, Synthesis 1 (1983)). Of course protic or enolizable solvents must be avoided. Preferably the silylation reaction is carried out with SiMe₃Cl in the presence of LDA or Li-HMDS in a mixture of THF and solvents of the pentane, hexane, cyclohexane, heptane, toluene type.

The arylation reaction by coupling of the organometallic of formula $R_5MgHal$, $R_5Li$ or $(R_5)_2CuLi$ with the silylated derivative of formula (II) is carried out according to the standard conditions known to a person skilled in the art. This arylation is preferably carried out with an organometallic derivative $R_5MgBr$ in THF alone or in a mixture (e.g. hexane, toluene, dichloromethane) in the presence of cuprous chloride (CuCl) or other copper (I) or (II) salts (such as: CuOAc, CuBr, $Cu(OAc)_2$, $CuCl_2$) in order to form the cuprate in an intermediate fashion. The preparation of the organomagnesium derivatives from the corresponding halogenated derivative is carried out in an aprotic medium in an oxygenated solvent such as ether or THF.

After treatment, an intermediate alcohol of formula (III') is formed, which is generally not isolated and of which the two protective groups of the keto functions in positions 17 and 3 are cleaved by standard methods, generally by hydrolysis in an acid medium and more particularly by the action of hydrochloric acid.

The aromatization reaction of the norsteroids is a standard reaction which is carried out in particular according to the methods described in EP 298,020. This aromatization can be carried out by catalysis with palladium or preferably in the presence of acetyl bromide and acetic anhydride. The deprotection of the acetyl group formed in position 3 is generally carried out in the presence of soda in methanol.

A more particular subject of the invention is a process as defined above characterized in that the silylated derivative is a trimethylsilyl derivative which makes it possible to obtain a silylated enol of formula (II) in which Ra, Rb and Rc each represent a methyl.

A quite particular subject of the invention is a process as defined above characterized in that the silylated derivative is $SiMe_3Cl$.

A quite particular subject of the invention is a process as defined above characterized in that the silylation reaction is carried out in the presence of LDA or Li-HMDS.

A more particular subject of the invention is a process as defined above characterized in that an organometallic derivative of formula $R_5$—MgBr is used.

A quite particular subject of the invention is a process as defined above, characterized in that an organometallic derivative of formula $R_5$—MgBr is used in which:

either $R_1$ and $R_2$, identical or different, represent a linear or branched alkyl radical containing from 1 to 4 carbon atoms or $R_1$ and $R_2$ form together with the nitrogen atom to which they are linked a

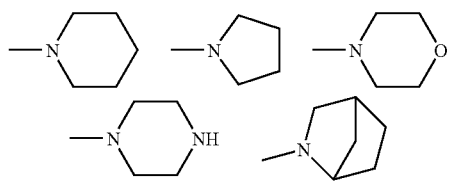

group, n is an integer comprised between 2 and 5, in order to obtain a corresponding compound of formula (III') then (IV).

A more particular subject of the invention is a process as defined above characterized in that the deprotection agent used on the compound of formula (III') in order to obtain the compound of formula (IV) is an agent allowing an acid hydrolysis and in particular hydrochloric acid.

A more particular subject of the invention is a process as defined above characterized in that the aromatization agent is acetyl bromide in the presence of acetic anhydride.

A quite particular subject of the invention is a process as defined above characterized in that a compound of formula (II) is treated with $SiMe_3Cl$ in the presence of a base in order to obtain the silylated enol of formula (IIIa):

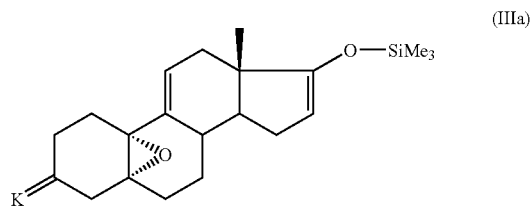

(IIIa)

which is reacted with an organocuprate derivative derived from an organometallic of formula $R_5$—MgHal in which n is an integer equal to 2 to 5 and either $R_1$ and $R_2$, identical or different, represent a linear or branched alkyl radical containing from 1 to 4 carbon atoms or $R_1$ and $R_2$ form together with the nitrogen atom to which they are linked a

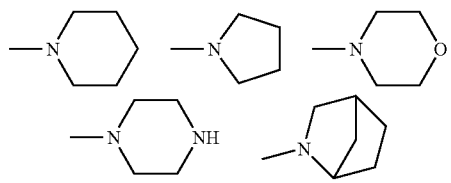

group, in order to obtain an isolated or non-isolated compound of formula (III'a)

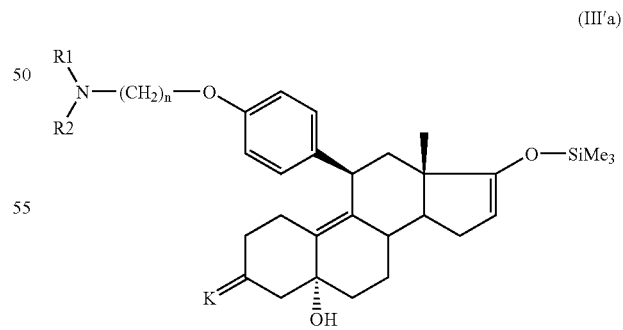

(III'a)

which is subjected to acid hydrolysis, in order to obtain the corresponding compound of formula (IV).

A subject of the invention is also a process as defined above characterized in that the compound of formula (I) is used as an intermediate product for the preparation of a derivative having an estrogen activity of formula (Ia):

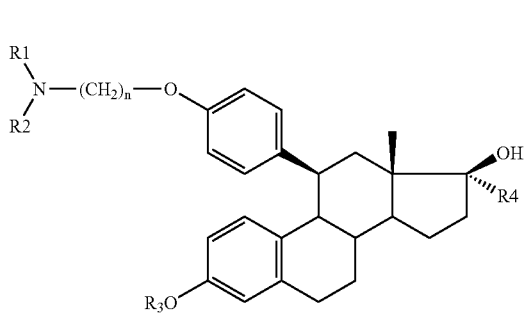

(Ia)

by the action of an organometallic alkylation agent of $R_4M$ type, $R_4$ being an alkyl radical containing from 1 to 4 carbon atoms non-substituted or substituted by one or more halogen atoms and M representing Mg-Hal or Li.

A quite particular subject of the invention is a process as defined above characterized in that $R_1$ and $R_2$ represent an alkyl radical containing from 1 to 4 carbon atoms or form together with the nitrogen atom which carries them a saturated heterocycle chosen from

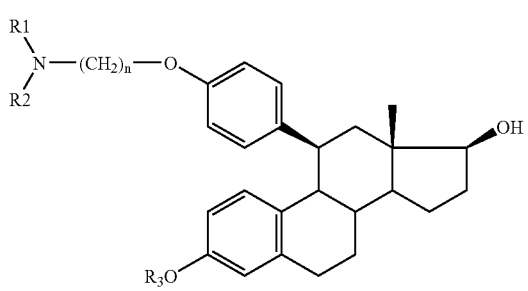

n is an integer equal to 2 to 5 and $R_3$ is a hydrogen atom and $R_4$ is a methyl.

A quite particular subject of the invention is a process as defined above characterized in that the alkylation agent is MeMgBr in the presence of cerium chloride.

A subject of the invention is also a process as defined above characterized in that the compound of formula (I) is used such as an intermediate product for the preparation of a derivative having an estrogen activity of formula (Ib):

(Ib)

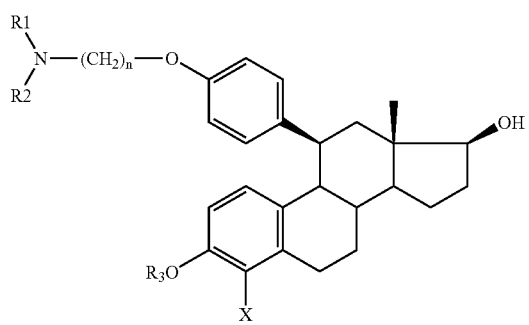

by the action of a ketone reducing agent.

A more particular subject of the invention is a process as defined above characterized in that $R_1$ and $R_2$ represent an alkyl radical containing from 1 to 4 carbon atoms or form together with the nitrogen atom which carries them a saturated heterocycle chosen from

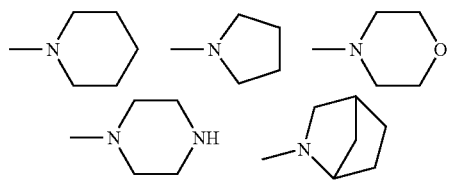

n is an integer equal to 2 to 5 and $R_3$ is a hydrogen atom.

A quite particular subject of the invention is a process as defined above characterized in that the reducing agent is $NaBH_4$.

The compounds of formulae (I) and (Ib), as defined previously, in which n is an integer equal to 5, $R_3$ is a hydrogen atom and $NR_1R_2$ represents a pyrrolidine or a piperidine are new and are therefore a subject of the present Application. They are active vis-à-vis the estrogen receptor, have a dissociated activity and a useful cardiovascular activity.

Therefore a subject of the invention is also the compounds of formulae (I) and (Ib), as defined above as medicaments, in particular for the prevention or treatment of osteoporosis, as well as the pharmaceutical compositions containing at least one medicament as defined above and a pharmaceutically acceptable vehicle.

A subject of the invention is also a process as defined above characterized in that the compound of formula (I) is used as an intermediate product for the preparation of a derivative having an estrogen activity of formula (Ic):

(Ic)

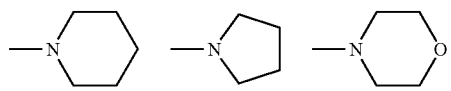

by the action a) of a halogenation reagent then b) of a ketone function reducing agent in position 17 or a) of a ketone finction reducing agent in position 17 then b) of a halogenation reagent.

A more particular subject of the invention is a process as defined above characterized in that $R_1$ and $R_2$ represent an alkyl radical containing from 1 to 4 carbon atoms or form together with the nitrogen atom which carries them a saturated heterocycle chosen from -continued

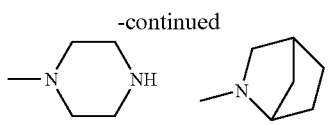

n is an integer equal to 2 to 5 and $R_3$ is a hydrogen atom and X is a chlorine atom.

A quite particular subject of the invention is a process as defined above characterized in that the halogenation agent, making it possible to introduce the halogen in position 4 of the steroid is N-chlorosuccinimide or N-bromosuccinimide, chlorine or bromine in an acid medium and the reducing agent is sodium borohydride. Generally the halogenation reaction is carried out before the reduction.

A subject of the invention is also a process for the preparation of the compounds of formula (III) from the compounds of formula (II) according to the method as defined above.

A subject of the invention is also a process for the preparation of the compounds of formula (IV) from the compounds of formula (III) according to the method as defined above.

A subject of the invention is also a process for the preparation of the compounds of formula (I) from the compounds of formula (IV) according to the method as defined above.

The compounds of formula (II) are known and their preparation is described in EP97572 (pages 23, 34), in FR95149 or also in J. Chem. Soc. Perkin Trans (1990) 11 3045-3048.

Certain compounds of formula (IV) are specifically described in FR2640977 ($NR_1R_2$= morpholine, piperidine and n=2).

The compounds of formula (I) are generally known and described in the following patents: EP-B-0097572, FR-B-2640977 and EP-B-305942.

A subject of the invention is also, as intermediate compounds, the compounds of formulae (III), (III') and (IV) it being understood that the compounds of formula (IV) in which $NR_1R_2$ represents a pyrrolidine and n is an integer equal to 2

$NR_1R_2$ represents a morpholine group and n is an integer equal to 2 are excluded.

The compounds of formula $R_5$—M are prepared according to the standard methods of organic chemistry from the corresponding halogenated derivative $R_5$-Hal. Generally the Grignard reagents are prepared in situ before the arylation reaction and converted to cuprate in situ, catalytically in the presence of CuCl.

The halogenated derivatives of formula $R_5$-Hal are known or generally prepared by the action of a chloroamine of formula $R_1R_2N$—$(CH_2)_n$—Cl with parabromophenol in a basic medium.

Experimental Part

Preparation 1

Aryl bromide of Formula $R_5$-Hal:(4-(2-(1-piperidinyl)ethoxy)1-bromobenzene).

A 30% aqueous solution of sodium hydroxide (MW: 40.0; 170 g; 2.2 eq.) was added to a solution under stirring of 4-bromophenol (MW: 173.0; 10 g; 0.578 mole), 1-piperidino-2-chloroethyl hydrochloride (MW: 184.1; 117 g; 1.1 eq.), and TEBAC (triethylbenzylammonium chloride; 10 g) in dichloromethane (600 ml) at 20° C. The mixture is stirred vigorously at 30-35° C. for 18 hours. The mixture is then diluted in water, and the organic phase is decanted, washed with water, dried over sodium sulphate and concentrated under vacuum to dryness (162 g yellow oil; yield: 98.5%; purity (CG): 98%): $C_{13}H_{18}BrNO$; MW: 284.2;

IR ($CHCl_3$, $cm^{-1}$): 1591, 1579, 1489 $cm^{-1}$

NMR $^1H$ ($CDCl_3$, ppm): 1.44 (m, 2H); 1.59 (m, 4H); 2.48 (m, 4H); 2.75 (t, J=6 Hz, 2H); 4.06 (t, J=6 Hz, 2H); 6.78 and 7.35 (AA'BB', 4H)

MS (ES+m/z): 284 ($M^+$) 111.85

Preparation 2

Aryl bromide of Formula $R_5$-Hal: (4-(5-(1-pirrolidinyl)penthoxy) 1-bromobenzene) hydrochloride and its base.

A mixture constituted by 1,5-dibromopentane (6.92 g; 30 mmoles), methylethylketone (9.2 ml) and potassium carbonate (2.07 g; 15 mmoles) is taken to reflux then 4-bromophenol (2.62 g; 15 mmoles) is added over 1 hour under reflux. The reaction medium is maintained for 4 hours under reflux then potassium carbonate (3.1 g; 22.5 mmoles) is added and over 15 minutes pyrrolodine (3.13 ml; 37.5 mmoles). The reaction medium is again taken to reflux for 20 minutes, cooled down to ambient temperature, filtered and the solvent is evaporated off under reduced pressure. A yellow oil is obtained which is diluted with ethyl acetate (21 ml), water (27.5 ml) and salt water (2.5 ml), followed by decanting, extraction with ethyl acetate and acidification with 3N hydrochloric acid (7.5 ml). After stirring at 0-5° C., crystallization is observed. The crystals are washed, dried under vacuum at ambient temperature and 3.13 g of expected product is obtained in the form of the hydrochloric acid salt (MP=130° C. then 138° C.).

NMR $^1H$ ($CDCl_3$, ppm): 1.56 (m, 2H); 1.82 (m, 2H); 1.98 (m, 2H); 2.14 (bs, 4H); 2.80 (bs, 2H); 3.05 (m, 2H); 3.76 (bs, 2H); 3.93 (t, 2H); 6.76 and 7.36 (AA'BB', 4H); 12.24 (bs, 1H).

MS (EI; m/z): 311($M^+$), 310, 140, 84, 38, 36.

The base is obtained by dissolving 22 g of the hydrochloride in 88 ml of dichloromethane then adding 110 ml of 10% potassium carbonate in water. After stirring at ambient temperature, decanting, and extraction with dichloromethane, the organic phases are dried, filtered and evaporated under reduced pressure until an oil is obtained which is taken up in 88 ml of heptane. After filtration, rinsing and concentration to dryness, 19.5 g of expected product (oil) is obtained. Yield: 54%.

NMR $^1H$ ($CDCl_3$, ppm): 1.42-1.64 (m, 4H); 1.72-1.85 (m, 6H); 2.41-2.53 (m, 6H); 3.91 (t, 2H); 6.76 and 7.35 (AA'BB', 4H).

MS (EI; m/z): 311($M^+$), 172, 155, 140, 84.

Preparation 3

4-(5-(1-pirrolidinyl)penthoxy)1-bromobenzene magnesium

A solution of aminoaryl bromide (P2) (8 g, 25.6 mmoles) in THF (12 ml) is added, over 40 minutes, after initiation, whilst maintaining the temperature at approximately 60° C., to a suspension under nitrogen of magnesium turnings (686 mg, 28.2 mmoles) in THF (2 ml). Stirring is carried out for one hour at 60° C. followed by cooling down to ambient temperature. In this way an approximately 1 M suspension of aminoarylmagnesium in THF is obtained which is then used for the preparation of the product of Example 2 (Stage b).

Preparation 4

Dehydration of cerium trichloride heptahydrate.

Cerium trichloride heptahydrate is heated under vacuum under stirring from 20 to 140° C. at 10-20 Torr over 4 hours, then at 140° C. at 10-20 Torr over 11 hours, followed by cooling down under an argon atmosphere.

EXAMPLE 1

17-alpha-methyl-11-beta-(4-(2-(1-piperidinyl)ethoxy)phenyl)-estra-1,3,5(10)-triene-3,17-beta-diol Stage a: 3,3-ethylenedioxy-5,10-alpha-epoxy-estr-9(11)-ene-17-one. (compound of formula (II))

3,3-ethylenedioxy-estra-5(10), 9(11)-diene-17-one (50 g; M: 314.4; 0.159 mole), hexachloroacetone (98%; 2.5 ml; 0.1 eq.), pyridine (0.25 ml), 50% hydrogen peroxide (approx. 18 M; 15 ml; 1.7 eq) and dichloromethane (250 ml) are mixed vigorously over 18 hours at 20-25° C. After reduction in the presence of aqueous metabisulphite, washing (water) and extractions (dichloromethane), the organic phase is concentrated to a total volume of approximately 200 ml. Then the dichloromethane is replaced with ethyl acetate by continuous distillation to a constant volume, until the internal temperature reaches 77° C. The mixture is cooled down to 30° C. and a spontaneous crystallization of the epoxide is observed. The suspension is cooled down to 0° C. and stirred for 1 hour, then the product is filtered and dried under vacuum over 18 hours at 40° C. (22.5 g white solid; yield: 42.8%; HPLC purity: 93%): $C_{20}H_{26}O_4$; MW: 330.4;

IR ($CHCl_3$, $cm^{-1}$): 1733, 1636

NMR $^1$H ($CDCl_3$, ppm): 0.88 (s, 3H); 3.94 (m, 4H); 6.05 (m, 1H).

Stage b: Silylated enol ether 3: 3,3 ethylenedioxy-5,10-alpha-epoxy-17-trimethylsilyloxy-estra-9(11), 16(17)-diene.

N-butyllithium (1.6 M solution in a mixture of hexanes; 400 ml; 1.06 eq.) was added over 20-30 minutes to a solution under stirring of diisopropylamine (M: 101.2; d: 0.714; 100 ml; 1.17 eq.) in anhydrous THF (600 ml), at −10° C. A solution of epoxide prepared in Stage A (200 g; 0.605 mole) in THF (1.3 L) was added over 30-40 minutes at −10° C., and the mixture was stirred for 15 minutes at −10° C. Trimethylchlorosilane (M: 108.6; d: 0.856; 100 ml; 1.3 eq.) was added over 20-30 minutes at −10° C., and the mixture was stirred for 3 hours at approximately 13° C., then concentrated under vacuum to a final volume of approximately 400 ml. The solvents were then replaced with toluene to a constant volume at 30° C. max. The salts were then eliminated by filtration then washed with toluene. The filtrate was concentrated to dryness under vacuum which produces the expected product 3 in the form of a white solid (252 g): $C_{23}H_{34}O_4Si$; MW: 402.6;

IR ($CHCl_3$, $cm^{-1}$): 1621, 1254, 849

NMR $^1$H ($CDCl_3$, ppm): 0.19 (s, 9H); 0.80 (s, 3H); 3.85-4.00 (m, 4H); 4.47 (dd, J=1.5 and 1 Hz, 1H); 6.03 (m, 1H)

MS (m/z): 402 ($M^+$), 387 ($M^+$—$CH_3$), 99

Stage c: 11-beta-(4-(2-(1-piperidinyl)ethoxy)phenyl)-estra-4,9-diene-3,17-dione.

20 ml of a solution of aryl bromide P1 (296 g; MW=284.2; 1.72 eq.) in THF (1 L) is added to a suspension of magnesium (turnings; MW=24.3; 28 g; 1.9 eq.) in THF (60 ml) at 20-22° C. under stirring. The mixture is stirred at approximately 60° C. until Grignard's reagent (exothermic; grey colour) is formed. The remainder of the solution is then added carefuilly over approximately 90 minutes at approximately 60° C., and the suspension is stirred for 60 minutes at the same temperature, then left to cool down. Cuprous chloride (MW=99.0; 6 g; 0.10 eq.) is added at 20° C. and the suspension is cooled down to approximately −5° C. The silylated enol ether as prepared above (0.60 moles) is diluted with THF (600 ml) and this solution is added over 1 hour at approximately −5° C. to the mixture of Grignard's reagents and cuprate formed in situ. The mixture is stirred for 1 hour at approximately 0° C., then poured into a biphasic mixture of ammonium chloride (600 g) in water (4 L), followed by extraction with dichloromethane. The organic phase is then washed with water and concentrated under vacuum. Dichloromethane (1.2 L) and water (600 ml) are added. The mixture is cooled down to 0-5° C. and 36% hydrochloric acid (300 ml; 5.8 eq.) is added over 30 minutes. The biphasic system is stirred vigorously for 2 hours at approximately 12° C. The organic phase is decanted and washed with water. The secondary amine products are eliminated in the acid aqueous phase whilst the hydrochloric acid salt of enone 4 remains in the dichloromethane. The organic phase is neutralized with aqueous sodium hydrogen carbonate, washed with water then concentrated until a final volume of approximately 600 ml is obtained. The dichloromethane is replaced by diisopropyl ether at 40-45° C. to a constant volume. The expected enone crystallizes, and is filtered at 20-22° C. then dried under vacuum at 35-40° C. (236 g white solid; yield: 82.3%; (from epoxide 2): $C_3H_{39}NO_3$; MW: 473.7;

IR ($CHCl_3$, $cm^{-1}$): 1735, 1658, 1609, 1581, 1509

NMR $^1$H ($CDCl_3$, ppm): 0.56 (s, $CH_3$); 2.50 (m, 4H); 2.75 (t, J=7 Hz, 2H); 4.06 (t, J=7 Hz, 2H); 4.37 (bs, J=7 Hz, 1H); 5.79 (bs, 1H); 6.82 and 7.07 (AA'BB', 4H)

Stage d: 11-beta-(4-(2-(1-piperidinyl)ethoxy)phenyl)-estra-1,3,5(10)-trien-3-ol-17-one.

Acetic anhydride (MW=102.1; d=1.09; 30 ml; 3.1 eq.) and acetyl bromide (MW=123.0; d=1.66; 30 ml; 3.9 eq.) are added to a solution of enone prepared in the previous stage (50 g; 0.105 moles) in dichloromethane (200 ml), at 20-25° C. (exothermic addition). The brown solution is stirred for 5 hours at 20-25° C. then carefully poured into a suspension of sodium hydrogen carbonate (120 g) in water (500 ml) (release of carbon dioxide). The mixture is stirred vigorously overnight at 20-25° C., then the organic phase is washed with water then concentrated to a final volume of 150 ml. The dichloromethane is replaced by methanol to a constant volume by distillation under progressive vacuum at approximately 40° C. The saponification of the estrone acetate is carried out by the addition of a solution of potassium hydroxide (MW=56.0; 8.85 g; 1.5 eq.) in methanol (100 ml) at 0-5° C. The mixture is mixed for 1.5 hours at 0-5° C., then poured into water (250 ml) and dichloromethane (250 ml). The organic phase is washed with water. Water and 36% hydrochloric acid (22.5 ml; 2.5 eq.) are added. The organic phase is dried over sodium sulphate, filtered and concentrated until a final volume of 250 ml is obtained. The residual methanol is replaced with dichloromethane to a constant volume by azeotropic distillation. The arylestrone hydrochloride crystallizes spontaneously and is filtered at 0° C., but not dried. Dichloromethane (400 ml) as well as a solution of potassium carbonate (MW=138.2; 13.6 g; 0.94 eq.) in water (200 ml) are added to the solid at 20-22° C. The mixture is stirred until dissolution, then the organic phase is decanted, washed with water and concentrated until a final volume of 250 ml is obtained. Acetone (500 ml), then silica gel (Merck Si 60; 50 g) are added at 20-22° C. The suspension is stirred for 1 hour at 20-22° C., and the silica is eliminated by filtration and washed with a mixture of acetone and dichloromethane 2/1. The filtrate is concentrated to 400 ml, and the solvent is replaced by isopropyl ether to a constant volume (final T: 68° C.). The arylestrone 5 crystallizes during distillation and is filtered at 20-22° C., then dried under vacuum at 40-50° C. (36.9 g white solid;

yield: 74.4% with respect to the dry substance; HPLC purity: 99.9%): $C_{31}H_{39}NO_3$; MW: 473.7;

IR ($CHCl_3$, $cm^{-1}$): 3598, 1732, 1610, 1580, 1512

NMR 1H ($CDCl_3$, ppm): 0.49 (s, 3H); 3.90-4.05 (m, 3H); 6.38 (dd, J=8.5 and 2.5 Hz, 1H); 6.44 (bs, 1H); 6.80 (d, J=8.5 Hz, 1H); 6.44 and 6.95 (AA'BB', 4H)

MS (m/z):($FAB^+$; m/z): 474 ($MH^+$), 112, 98

Stage e: 17-alpha-methyl-11-beta-(4-(2-(1-piperidinyl) ethoxy)phenyl)-estra-1,3,5(10)-triene-3,17-beta-diol).

A suspension of 39 g of cerium trichloride (dehydrated as described above (preparation 4); water: 1.1%; MW=246.5; 3.0 eq.) in THF (500 ml) is stirred under reflux (67° C.) for 2 hours, then cooled down to 20-22° C. Methylmagnesium chloride (3M solution in THF; 70 ml; 4.0 eq.) is added over 15-20 minutes at 20-22° C. The grey suspension is stirred for 1 hour at 20-22° C. A solution of arylestrone 5 (25 g; 52.8 mmole) in THF (100 ml) is added over 15-20 minutes at 20-22° C., and the mixture is stirred for 1.5 hours at 20-22° C. Acetone (MW=58.1; d=0.79; 16 ml; 4.1 eq) is added over 15-20 minutes at 20-22° C. The mixture is stirred for 15 minutes at 20-22° C., then poured into a saturated aqueous mixture of ammonium chloride (250 ml), water (250 ml) and ethyl acetate (500 ml) under stirring. The organic phase is washed with aqueous ammonium chloride, dried over sodium sulphate and concentrated under reduced pressure. The white solid is dissolved in methanol (75 ml) at 45-50° C., and the solution is acidified to pH 5.5 by the addition of aqueous 36% hydrochloric acid, at 33-37° C. The methyl arylestradiol hydrochloride crystallizes after cooling down. The suspension is stirred for 30 minutes at 20-22° C., then ethyl acetate (500 ml) is added; the hydrochloride is filtered at 0-2° C. and dried under vacuum at 40° C. (27.2 g white solid; yield: 98% (85.4% with respect to dry substances); HPLC purity: 99.9%; solvation: 13%): $C_{32}H_{44}ClNO_3$; MW: 526.2. The methyl arylestradiol hydrochloride (20 g) is dissolved in methanol (100 ml) at 50-52° C., then water (200 ml) is added at the same temperature. The pH is adjusted to 5.6-6.0 by the addition of an aqueous solution (3.3%) of potassium carbonate. The solution is concentrated to a final volume of 200 ml, then the methanol is replaced by water to a constant volume (final T=97° C.). Under these conditions, the anhydrous hydrochloride crystallizes during cooling down to 80° C., and is stirred for 30 minutes at 80-82° C. It is very important to obtain the anhydrous form in this fashion; otherwise, imperfect forms of methyl arylestradiol can be obtained after neutralization. The hydrochloride is neutralized by the addition over 30 minutes at 80-82° C. of an aqueous solution of potassium carbonate at 3.3% (approximately 120 ml). The suspension is stirred for 4 hours at 80-82° C. in order to complete the conversion of the anhydrous hydrochloride to methyl arylestradiol hydrate. The white solid is filtered at 20-22° C., washed with water and dried under vacuum at 35-40° C. Weight: 16.9 g; total yield: 86.1% with respect to the dry substances; HPLC purity: 99.8%, solvation: 3.6% water; $C_{32}H_{43}NO_3$; MW: 489.7;

IR ($CHCl_3$, cm-1): 3602, 1610, 1580, 1512

NMR 1H ($CDCl_3$, ppm): 0.51 (s, 3H); 1.29 (s, 3H); 3.98 (m, 3H); 6.41 (m, 2H); 6.78 (d, J=8 Hz, 1H); 6.41 and 6.94 (AA'BB', 4H)

MS (FAB+; m/z): 490 ($MH^+$), 112, 98

EXAMPLE 2

Stage a: Arylation
11-beta-(4-(2-(1-pirrolidinyl)pentoxy)phenyl)-estra-4,9-diene-3,17-dione The silylated derivative obtained in Example 1 Stage b, (13 mmoles) in THF (13 ml) is mixed with cuprous chloride (130 mg), cooled down to approximately 5° C. and 16 ml of the magnesium compound (P3) is added over 10 minutes. The reaction medium is maintained at 0° C. for 1 hour, then the mixture constituted by ice (43 g), water (43 ml), $NH_4Cl$ (26 g) and dichloromethane (43 ml) is added, followed by stirring for 5 minutes, washing, extraction with dichloromethane, drying, filtration and evaporation under reduced pressure (compound of formula (III')).

The dry extract is diluted in dichloromethane (26 ml), water is added (13 ml), followed by cooling down to approximately 2° C., 12N hydrochloric acid at 37% is added (6.3 ml) and the reaction medium is stirred for one hour at approximately 2° C. After washing with water, and extraction with dichloromethane, the organic phases are poured into a saturated aqueous solution of $NaHCO_3$ (21 ml), followed by stirring, reextracting with dichloromethane, drying, filtering and evaporating under reduced pressure until 8.84 g of crude product is obtained in the form of an oil which is crystallized from isopropyl ether. After filtration, 4.93 g of expected product is obtained. Yield: 75.6%; $C_{33}H_{43}NO_3$; MW: 501.7; MP=166° C.; MS (ES+; m/z): 502 ($MH^+$)

Stage b: Aromatization
3-acetoxy-11-beta-(4-(2-(1-pirrolidinyl)pentoxy)phenyl)-estra-1,3,5(10)-trien-17-one (non-isolated)
11-beta-(4-(2-(1-pirrolidinyl)pentoxy)phenyl)-estra-1,3,5 (10)-trien-3-ol-17-one (isolated)

Acetic anhydride (0.57 ml, 6 mmoles) and acetyl bromide (0.57 ml, 7.5 mmoles) are added to a solution of the enone prepared in the previous stage (1 g, 2 mmoles) in dichloromethane (4 ml), at ambient temperature and stirring is carried out for 3.5 hours at ambient temperature. Then the reaction medium is poured into a solution of $NaHCO_3$ (2.18 g, 26 mmoles) in water (10 ml), followed by washing with 1N soda (5 ml) and water, reextracting with dichloromethane, drying filtering and concentrating under reduced pressure.

After dilution in methanol (9 ml), potassium hydroxide in pellets (168 mg; 3 mmoles) is added, at approximately 0° C., followed by stirring for 45 minutes at approximately 0° C. and under bubbling through with nitrogen. Then dichloromethane and water are added, followed by stirring for 5 minutes, washing with water, reextracting with dichloromethane, drying, filtering and evaporating under reduced pressure. 800 mg of expected product is obtained. Yield: 80%; $C_{33}H_{43}NO_3$; MW: 501.7;

IR ($CHCl_3$, $cm^{-1}$): 3598, 1732, 1610, 1580, 1512

NMR $^1$H ($CDCl_3$, ppm): 0.47 (s, 3H); 1.79 (m, 4H); 2.55 (m, 4H); 3.90 (t, 2H); 3.98 (bt, 1H); 6.35 (dd, 1H); 6.57 (d, 1H); 6.79 (d, 1H); 6.59 and 6.95 (AA'BB', 4H)

Stage c: Reduction
11-beta-(4-(2-(1-pirrolidinyl)-pentoxy)phenyl)-estra-1,3, 5(10)-trien-3,17-beta-diol 600 mg of the ketone prepared in the previous stage (1.2 mmol) is dissolved in 6 ml of methanol, cooled down to 0° C. and 95% $NaBH_4$ (62 mg, 1.5 eq.) is introduced by fractions. After 2 hours, acetone (0.5 ml) is added, followed by stirring for 5 minutes, then dichloromethane (6 ml) and water (6 ml) are added. Following decanting, washing with water, and reextracting with dichloromethane, the organic phases are collected, dried over $Na_2SO_4$, filtered and evaporated under reduced pressure in order to obtain 590 mg of expected alcohol. Yield: 98%; $C_{33}H_{45}NO_3$; MW: 503.7

IR ($CHCl_3$, $cm^{-1}$): 3604, 1610, 1580, 1512

NMR $^1$H ($CDCl_3$, ppm): 0.34 (s, 3H); 1.84 (m, 4H); 2.65 (m, 4H); 3.68 (m, 1H); 3.81 (t, 2H); 3.91 (bt, 1H); 6.36 (dd, 1H); 6.57 (d, 1H); 6.77 (d, 1H); 6.57 and 6.77 (AA'BB', 4H)

MS (EI, m/z): 503 ($M^+$), 362, 260, 140, 84.

EXAMPLE 3

11β-(4-(2-(diethylamino)ethoxy)phenyl)-estra-1,3,5(10)-trien-3-ol-17-one hydrochloride.

Acetic anhydride (7.8 ml; 1.1 eq) and acetyl bromide (14 ml; 2.5 eq.) are added to a solution of 11-beta-(4-(2-(diethylamino)ethoxy)phenyl)-estra-4,9-diene-3,17-dione obtained in an analogous manner to that of Example 1 Stage c but with 4-(2diethylamino)ethoxy) 1-bromobenzene (MW: 461.6; 35 g; 0.076 mole) in dichloromethane (140 ml), at 20-25° C. (exothermic addition). The brown solution is stirred for 5 hours at 20-25° C. then carefully poured into a solution of sodium hydrogen carbonate (84 g) in water (350 ml) (release of carbon dioxide). The mixture is stirred vigorously for approximately 18 hours at 20-25° C., then the organic phase is decanted, washed with water until all bromides are removed and concentrated to approximately 105 ml. The dichloromethane is replaced by methanol to a constant volume by distillation under vacuum at approximately 40° C. The estrone acetate is saponified by the addition of a solution of potash (6.37 g; 1.5 eq.) in methanol (70 ml) at 0-5° C. The medium is stirred for 1.5 hours at 0-5° C., then poured into water (175 ml) and dichloromethane (175 ml). The organic phase is washed with water until the bromides are removed. Water, methanol (if there is a decanting problem) and 36% hydrochloric acid (15.7 ml; 2.4 eq.) are added. The reaction medium is stirred, decanted and the organic phase dried over sodium sulphate, and concentrated to 175 ml. The solvents are driven off by distillation to a constant volume, by regular addition of 2-butanone (final T: 78° C.). The arylestrone hydrochloride crystallizes; it is filtered at 20-22° C., and dried under vacuum at 40-60° C. (34.0 g beige solid; yield: 89.9% HPLC purity: 98.7%; solvation: 12%): $C_{30}H_{40}ClNO_3$; MW: 498.1;

IR ($CHCl_3$, $cm^{-1}$): ν 3601, 2456, 1733, 1610, 1584, 1511;

NMR $^1$H ($CDCl_3$, ppm): δ0.42 (s, 3H), 1.31 (m, 6H), 3.16 (m, 4H), 3.31 (m, 2H), 3.96 (bt, 1H), 4.17 (m, 2H), 6.51 (m, 1H), 6.68 (m, 1H), 6.73 (m, 1H), 6.51 and 6.95 (AA'BB', 4H), 11.36 (bs; 1H);

MS (EI; m/z): 461 (M$^+$), 446, 362, 86, 38 and 36 (HCl).

4-chloro-11β-(4-(2-(diethylamino)ethoxy)phenyl)-estra-1,3,5(10)-trien-3-ol-17-one hydrochloride.

36% hydrochloric acid (4 ml; 0.47 eq) then, by fractions, N-chlorosuccinimide (12.6 g; 1.0 dry eq) are added to a solution of arylestrone hydrochloride prepared in the previous stage (50 g; 0.100 mole) in dichloromethane (250 ml) and methanol (250 ml) at approximately 10° C. (exothermic addition). The solution is stirred for 1 to 3 hours at 8-12° C. (the parasitic formation of 2-chloro and 2,4-dichloro derivatives is observed by HPLC). Treatment is carried out by carefully pouring into a solution of sodium thiosulphate (25 g) and 30% soda (14 ml; 1.5 eq) in water (500 ml), followed by extraction with dichloromethane (250 ml). The organic phase is decanted, and water and 36% hydrochloric acid (12.5 ml; 1.6 eq) are added to it, followed by decanting and extraction of the aqueous phases with a dichloromethane-methanol mixture. The organic phases are combined and dried over sodium sulphate and concentrated to 250 ml. The methanol is driven off by dichloromethane to a constant volume by azeotropic distillation (final T: 39.8° C.). The chloroarylestrone hydrochloride crystallizes; it is filtered at 20-22° C., and dried under vacuum at 40° C. (41.0 g white solid; yield: 77%; HPLC purity: 98.8%; solvation: 3%): $C_{30}H_{39}Cl_2NO_3$; MW: 532.6;

IR ($CHCl_3$, $cm^{-1}$): ν 1727, 1610, 1582, 1568, 1511, 1493;

NMR $^1$H ($CDCl_3$, ppm): δ0.45 (s, 3H), 1.41 (t, 6H); 3.21 (m, 4H), 3.37 (m, 2H), 3.99 (bt, 1H), 4.38 (m, 2H), 5.87 (OH), 6.68 (d, 1H), 6.78 (d, 1H), 6.60 and 6.94 (AA'BB', 4H), 12.30 (bs, 1H);

MS (ES$^+$; m/z): 498, 496 (MH$^+$).

The invention claimed is:
1. A process for the preparation of a compound of the formula

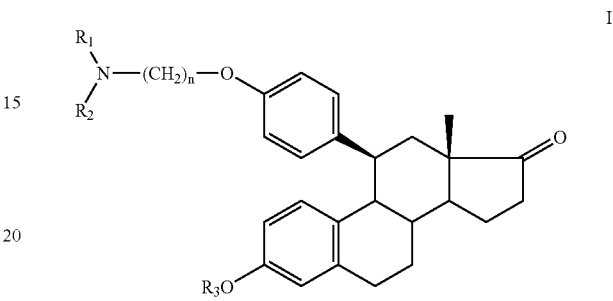

selected from the group consisting of
wherein either $R^1$ and $R^2$, are individually selected from the group consisting of benzyl, alkyl, alkenyl, and alkynyl of up to 8 carbon atoms and cycloalkyl of 3 to 8 carbon atoms or $R_1$ and $R_2$ form together with the nitrogen which carries them an aromatic or non-aromatic, saturated or unsaturated heterocycle of 5 to 6 ring members, optionally containing from 1 to 3 additional heteroatoms, and optionally connected to another ring, $R_3$ is hydrogen or a protective group of the hydroxy function, n is an integer from 2 to 8 comprising reacting a compound of the formula

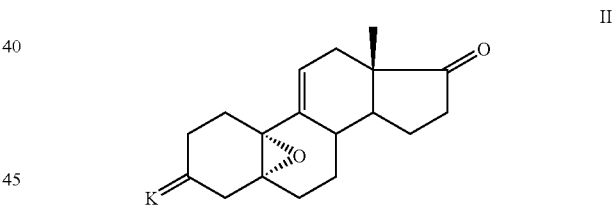

K is a protected ketone function
with a silylation agent in the presence of a base, to obtain a silylated enol of the formula

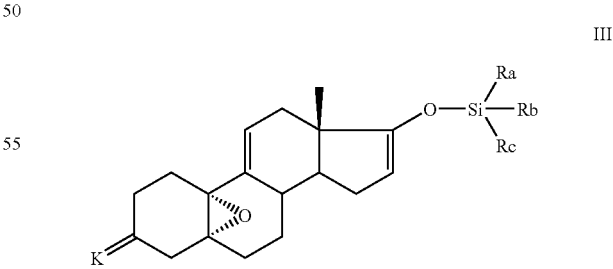

wherein Ra, Rb and Rc, are individually alkyl of 1 to 4 carbon atoms or phenyl,
reacting the said compound of formula III with
an organocuprate derivative, derived from the organometallics $R_5MgHal$ or $R_5Li$, Hal being halogen and generated in a catalytic or stoichiometric fashion, in which $R_5$ is

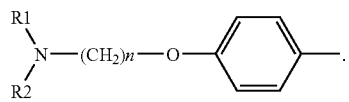

n, $R_1$ and $R_2$ being as defined above,
to obtain a compound of the formula which is isolated or non-isolated:

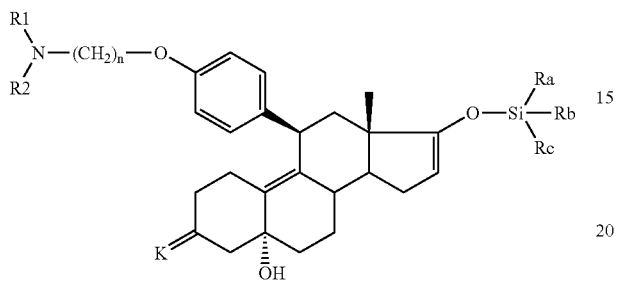

III' and then reacted with a deprotection agent
to obtain a compound of the formula:

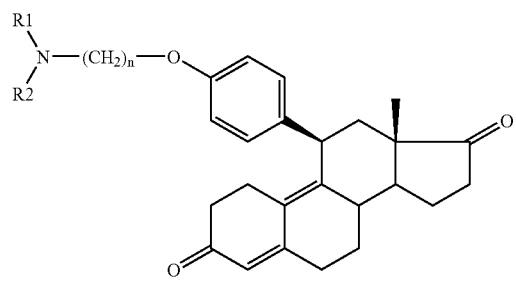

IV and reacting the latter with an aromatization agent to obtain the expected compound of formula (I) and optionally subsequently deprotecting to obtain a compound of formula (I) with $R_3$ is hydrogen.

2. The process of claim 1 wherein the silylated agent is trimethylsilyl derivative to obtain a silylated enol of formula (III) in which Ra, Rb and Rc are all methyl.

3. The process of claim 1 wherein the silylated agent is $SiMe_3Cl$.

4. The process of claim 1 wherein the silylation reaction is carried out in the presence of LDA or LiHMDS.

5. The process of claim 1 wherein an organometallic derivative of formula $R_5$-MgBr is used, $R_5$ being as defined in claim 1.

6. The process of claim 1 wherein an organometallic derivative of formula $R_5$-MgBr is used, $R_5$ being as defined in claim 1 and in which
either $R_1$ and $R_2$ are individually alkyl of 1 to 4 carbon atoms
or $R_1$ and $R_2$ form together with the nitrogen to which they are linked a member of the group consisting of

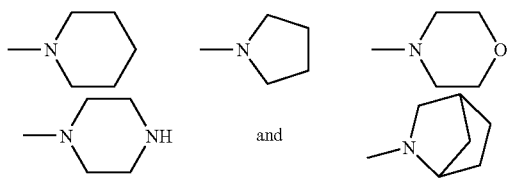

n is an integer between 2 and 5, to obtain a corresponding compound of formula (III') and then (IV).

7. The process of claim 1 wherein the deprotection agent used on the compound of formula (III') to obtain the compound of formula (IV) is an agent allowing acid hydrolysis.

8. The process of claim 1 wherein the aromatization agent is acetyl bromide in the presence of acetic anhydride.

9. The process of claim 1 wherein a compound of formula (II) is treated with $SiMe_3Cl$ in the presence of a base to obtain the silylated enol of the formula:

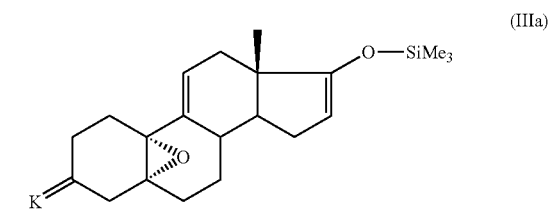

(IIIa)

which is reacted with an organocuprate derivative derived from of an organometallic of formula $R_5$-MgHal in which n is 2 to 5 and
either $R_1$ and $R_2$ are individually alkyl of 1 to 4 carbon atoms
or $R_1$ and $R_2$ form together with the nitrogen atom to which they are linked a member of the group consisting of

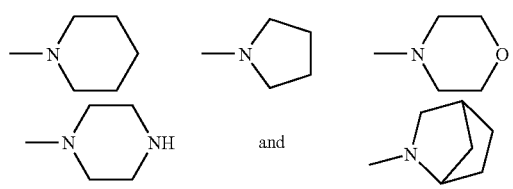

to obtain an isolated or non-isolated compound of the formula,

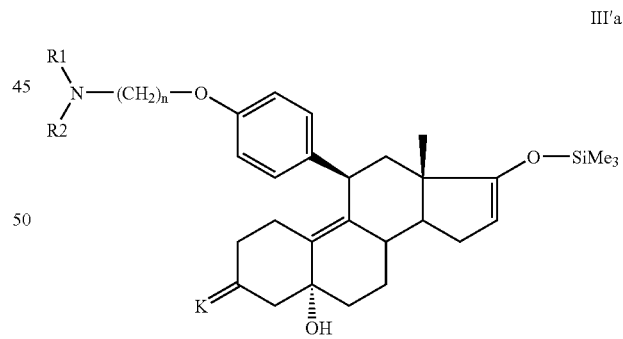

III'a which is subjected to acid hydrolysis, to obtain the corresponding compound of formula (IV).

10. A compound of formulae (I), as defined in claim 1, wherein n is 5, $R_3$ is hydrogen and $NR_1R_2$ is pyrrolidino or piperidino.

11. A method of treating osteoporosis in warm-blooded animals comprising administering to warm-blooded animals in need thereof a effective amount of a compound of claim 10 to treat osteoporosis.

* * * * *